(12) United States Patent
Pedersen et al.

(10) Patent No.: US 6,355,004 B1
(45) Date of Patent: Mar. 12, 2002

(54) URINARY CATHETER ASSEMBLY WITH INTEGRATED CATHETER APPLICATOR

(75) Inventors: Jens Kristian Pedersen, Hornbaek; Lars Bogelund Jensen, Copenhagen, both of (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/473,199

(22) Filed: Dec. 14, 1999

Related U.S. Application Data

(63) Continuation of application No. PCT/DK99/00639, filed on Nov. 19, 1999, and a continuation-in-part of application No. 09/218,306, filed on Dec. 22, 1998.

(30) Foreign Application Priority Data

Nov. 20, 1998 (DK) ......................................... 1998 01528

(51) Int. Cl.⁷ ................................................. A61D 5/00
(52) U.S. Cl. ..................................................... 600/581
(58) Field of Search .......................... 600/581, 29, 573, 600/575, 580; 604/262, 265, 171, 327, 349

(56) References Cited

U.S. PATENT DOCUMENTS

| | | | |
|---|---|---|---|
| 2,856,932 A | 10/1958 | Griffiths | 128/294 |
| 3,794,042 A | 2/1974 | DeKlotz | 128/349 R |
| 3,853,130 A * | 12/1974 | Sheridan | 604/171 |
| 3,898,993 A | 8/1975 | Taniguchi | 128/349 R |
| 4,140,127 A | 2/1979 | Cianci et al. | 128/349 R |
| 4,204,527 A | 5/1980 | Wu et al. | 128/762 |
| 4,246,909 A | 1/1981 | Wu et al. | 128/762 |
| 4,379,506 A | 4/1983 | Davidson | 206/364 |
| 4,955,879 A | 9/1990 | Mervine | 604/327 |
| 5,087,251 A | 2/1992 | Heyman et al. | 604/327 |
| 5,234,420 A | 8/1993 | Horton et al. | 604/327 |
| 5,263,946 A | 11/1993 | Klug | 604/327 |
| 5,454,798 A | 10/1995 | Kubalak et al. | 604/328 |
| 5,496,300 A | 3/1996 | Hirsh et al. | 604/327 |
| 5,531,724 A | 7/1996 | Young et al. | 604/327 |
| 5,643,236 A | 7/1997 | Hadley | 604/327 |
| 5,725,515 A | 3/1998 | Propp | 604/317 |
| 6,059,107 A * | 5/2000 | Nosted et al. | 604/265 |

FOREIGN PATENT DOCUMENTS

| | | |
|---|---|---|
| DK | Des. 0932 | 12/1986 |
| GB | 1493257 | 11/1977 |
| GB | 2284764 | 6/1995 |
| WO | WO94/06377 | 3/1994 |
| WO | WO97/26937 | 7/1997 |
| WO | WO98/11932 | 3/1998 |

* cited by examiner

Primary Examiner—Eric F. Winakur
Assistant Examiner—Brian Szmal
(74) Attorney, Agent, or Firm—Jacobson Holman, PLLC

(57) ABSTRACT

A urinary catheter assembly comprises at least one urinary catheter (1) and a flexible tubular catheter package comprising a hose member (4) narrowly surrounding the catheter (1). A proximal end of the catheter is connected with a connector member (3) and the package comprises a tubular compartment (10) connected with the hose member (4) for accommodation of the connector member (3). The compartment (10) is closed in a first end by a detachable cover member (11) and is detachably connected with the hose member (4). The compartment (10) is further formed with walls (14) of a thin flexible material, so that by removal of the catheter (1) and the compartment (10) from the hose member (4) the compartment (10) may be arranged on the catheter shaft for used as an applicator for safely guided introduction of the catheter into the urethra (15).

20 Claims, 6 Drawing Sheets

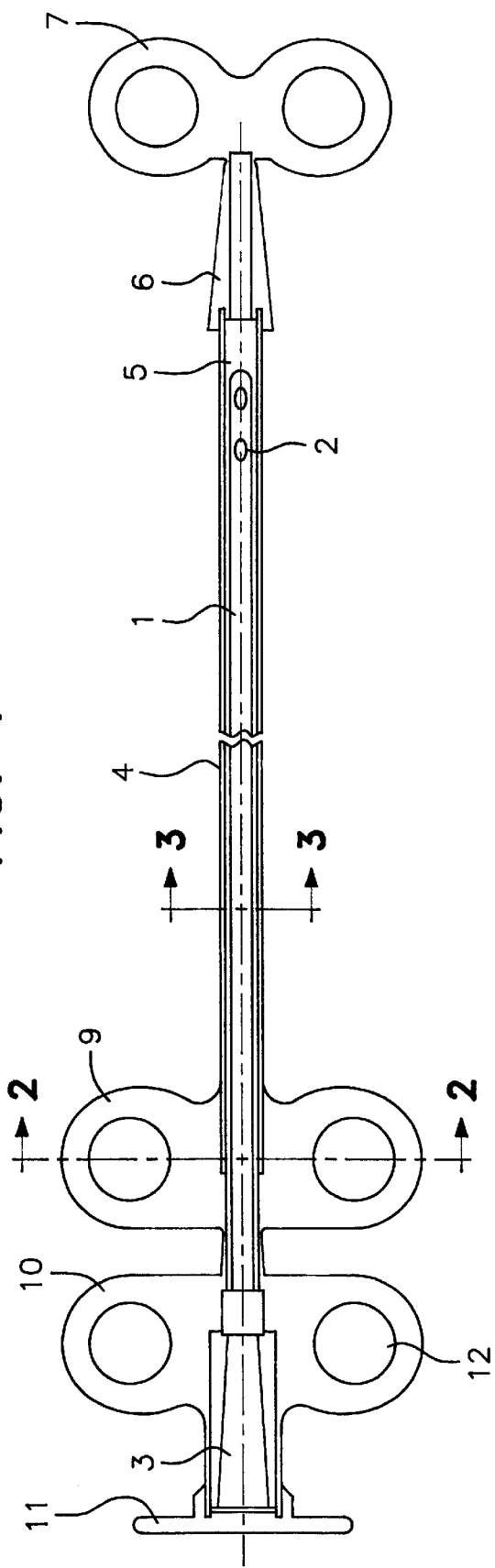
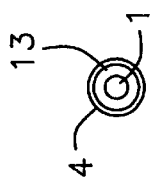
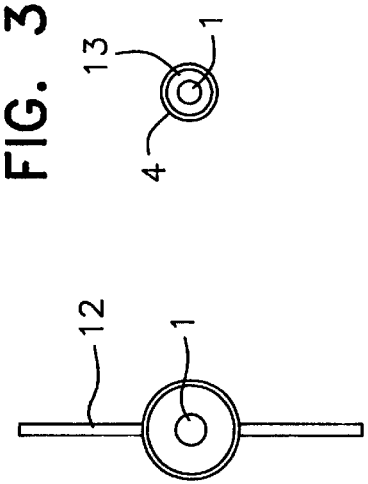

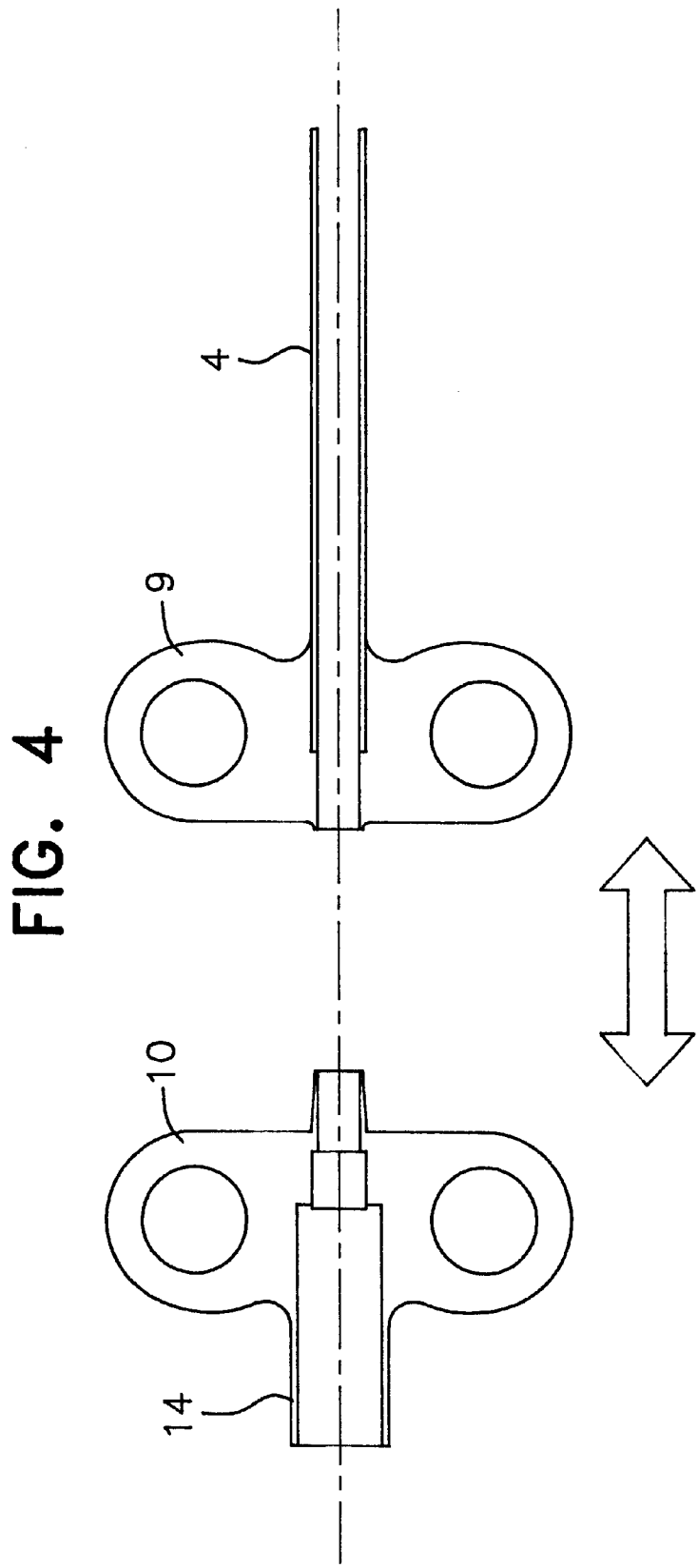

URINARY CATHETER ASSEMBLY WITH INTEGRATED CATHETER APPLICATOR

This application is a combined PCT continuation application of PCT/DK99/00639, filed Nov. 19, 1999, and Continuation-In-Part application of U.S. application Ser. No. 09/218,306, filed Dec. 22, 1998.

BACKGROUND OF THE INVENTION

1. Field of the Invention

The present invention relates to a urinary catheter assembly comprising at least one urinary catheter having a proximal end, and a flexible tubular catheter package comprising a hose member with a cavity narrowly surrounding said at least one catheter, the package further comprising a tubular compartment connected with said hose member for accommodation of said proximal end of the at least one catheter.

2. Description of the Related Art

Urinary catheters of the kind contemplated by the invention are increasingly used for so-called intermittent catheterization of the bladder. A typical use is for post-operative urine retention of newly operated patients in hospitals, for whom intermittent catheterization performed with intervals of 3 to 6 hours has brought a significantly reduced risk of infection of the urethra and the bladder compared to permanent catheterization.

Another typical use is with patients suffering from severe cases of urinary incontinence as for disabled individuals like para- or tetraplegics who frequently have no control permitting voluntary urination.

For such users intermittent catheterization have become increasingly common also in daily life situations outside the clinical environment of a hospital, whereby a significantly improved quality of life has been obtained for this group of patients.

For many such users it is necessary, however, to connect the catheter with a urine collection bag through a hose connected in one end with the bag and in the other end with the proximal terminal member of the catheter with the inherent disadvantage that several connecting operations must be performed prior to use of the catheter.

To overcome this problem it is known e.g. from GB-A-2,284,764, U.S. Pat. No. 2,856,932, U.S. Pat. No. 4,379,506, U.S. Pat. No. 4,204,527, U.S. Pat. No. 4,246,909, WO 94/06377, WO 97/26937 and Danish Design Registration No. 0932-1986 to integrate the catheter with the urine collection bag, typically by arranging the catheter inside the bag combined with a bag design permitting partly withdrawal of the catheter from the bag to provide a projecting catheter of a length sufficient for insertion through the urethra into the bladder.

Whereas catheter-bag combinations of this kind have undoubtedly facilitated the use of intermittent catheterization, they have not remedied the disadvantage associated with disposal of the collected urine.

In a disposable male urethral catheter assembly known from U.S. Pat. No. 4,246,909 the catheter-bag combination is made into a single integrated unit which is disposable after use. A catheter having an enlarged or bulbous discharge end is contained in a sterile environment in an upper chamber of a flexible bag. The upper chamber is detachably connected in one end with a lower sample chamber for collection of a urine sample and is partly defined in the opposite end by two chevrons defining an opening which is reduced in size relative to the enlarged discharge end of the catheter.

In use the penis is inserted into an open top of the bag outside the two chevrons and by manipulation of the upper chamber without touching the catheter a guided non-contaminating insertion of the catheter into the urethra may be effected, until the enlarged discharge end contacts the opening defined by the two chevrons, whereby the upper chamber forming a short extension in flow communication with the catheter will direct a urine sample flowing through the catheter to the lower sample chamber.

This disposable solution suffers, however, from significant cost disadvantages.

Guided non-contaminating insertion of a catheter into the urethra for intermittent catheterization of the bladder is further obtainable by use of a catheter assembly disclosed in applicants international patent application WO 96/30277 comprising a catheter placed in a package designed an functioning as an applicator for the insertion of the catheter. The package is composed of two plastic foil blanks joined in peeling zones along their edges. When the catheter is to be put in use the package is first opened at a distal end zone to expose the distal end of the catheter and subsequently gradual complete separation of the walls of the package is effected in a direction away from the distal end zone by pulling the walls of the package in opposite directions substantially perpendicular to the longitudinal direction of the package.

Although a more cost-effective solution is provided by this catheter assembly, practical experience has shown that some users such as elderly and disabled persons having a severely reduced dexterity may have difficulties with the applicator function of the package due to the pull force required to effect separation of the walls thereof.

SUMMARY OF THE INVENTION

On this background it is the object of the invention to provide a simple and relatively inexpensive catheter set permitting disabled users even when wheel chair bound to perform a safely guided non-contaminating insertion of the catheter.

To achieve this object a urinary catheter assembly according to the invention is characterized in that said compartment is closed in a first open end by a detachable cover member, whereas in a second opposite end it is detachably connected with said hose member, said compartment being further formed with walls of a thin flexible material so as to permit arrangement of said compartment on the at least one catheter for use as an applicator for guided non-contaminating insertion of the catheter into the urethra after detachment of said cover member and detachment of the compartment from the hose member.

By this design the compartment forming an integrated part of the package for the catheter in its supply condition may easily be broken-off and removed from the hose member and, after detachment of the cover member the compartment may be arranged on the catheter shaft. The thin flexible walls of the compartment may now be used as a finger grip applicator by being gently squeezed against the catheter by a moderate outside pressure.

In a preferred embodiment of the catheter assembly a further advantageous possibility may be obtained for using the hose member of the package as an extension of the catheter in flow communication therewith, so that urine drained from the bladder by intermittent catheterization may directed into a toilet or other available drainage means, is obtained by closing a distal end of the hose member remote from its connection with said compartment by a detachable closure, said proximal end of the at least one catheter being formed for connection with said distal end of the hose member such that after removal of said closure and detachment of said cover member, the hose member is connectable by its distal end with said proximal end of the at least one catheter to form an extension member in flow communication with the catheter.

Preferably, the proximal end of the at least one catheter is connected with a connector member. This design is particularly advantageous in combination with another embodiment of the invention, in which the distal end of the hose member is inseparably connected with a hose connector matching said connector member, said closure being detachably connected with said hose connector.

In another advantageous embodiment, the hose member is, at its proximal end, inseparably connected with an end member which is detachably connected with said compartment. Preferably, the detachable connection is provided by means of a weakening line, and the connection between the compartment and the end member may be re-established by twisting and/or pushing the compartment into the end member, the weakening line forming a substantially liquid-tight seal. By this design, it is possible to close the package after use in a simple manner.

The catheter assembly of the invention is suitable, in particular, for use with catheters having a hydrophillic surface coating throughout the part of their length intended for insertion into the urethra. Thus, in a further preferred embodiment the catheter is provided on at least a part of its surface with a hydrophillic surface coating intended to produce a low-friction surface character of the catheter by treatment with a liquid swelling medium prior to use of the catheter, and the package includes an amount of said liquid swelling medium sufficient for said treatment of the hydrophillic catheter surface coating. Since the hose member used as package for the catheter provided a cavity narrowly surrounding the catheter shaft, the amount of liquid swelling medium can be limited to what is needed for preparation of the hydrophillic coating.

By the integration of the amount of swelling medium needed for preparation of the hydrophillic surface coating in the catheter assembly, preparation of the hydrophillic surface coating is effected without separate treatment prior to use of the catheter. When removed from the hose member the catheter will immediately have the low-friction characteristics needed for its insertion into the urethra.

BRIEF DESCRIPTION OF THE DRAWINGS

In the following the invention will be explained in further detail with reference to the accompanying drawings, in which FIG. 1 is a longitudinal sectional view of an embodiment of the catheter assembly according to the invention in its supply condition;

FIGS. 2 and 3 are cross-sectional views along the lines II—II and III—III, respectively, in FIG. 1;

FIGS. 4 and 5 illustrate use of a part of the package for non-contaminating insertion of the catheter into a male urethra.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the embodiment shown in FIG. 1 the catheter assembly comprises one elongate urinary catheter 1 having a distal end, at which inlet openings 2 for inflow of urine are provided. In its opposite proximal end the catheter 1 is, in the embodiment shown, inseparably connected with a slightly conical connector member 3, which may be used for connection of the catheter with a standard hose connector for a drainage hose for the purpose of draining urine to suitable urine collection means such as a conventional flexible collection bag.

Figure 6:
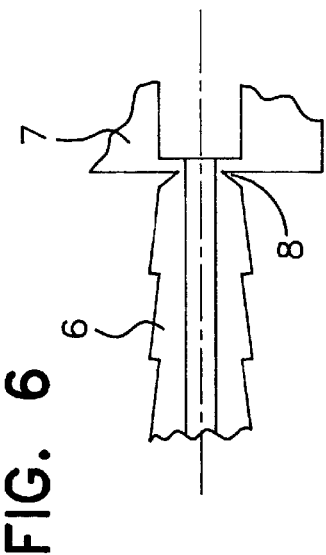
FIG. 6 is an enlarged view of a detachable closure member for the distal end of a hose member package in FIG. 1.

The catheter assembly further comprises a flexible tubular catheter package including a hose member 4 providing a cavity 5 narrowly surrounding the catheter 1. The hose member 4 is designed as a hollow body of any suitable material and may eg. comprise a film material. The interior cross-sectional dimensions of the hose member are chosen such that the cavity provided thereby may accommodate one or more catheters. At the distal end of the hose member 4 a detachable closure is provided which in the embodiment shown comprises a connector part 6 similar to a standard hose connector and inseparably connected with the distal end of the hose member 4 and a break-off closure part 7. As shown in FIG. 6 the connector part 6 may be profiled at its external side to provide a sealed connection with the connector member 3 at the proximal end of catheter 1 and may be connected with the break-off closure part 7 through a notch-like incision 8 providing for easy breaking-off of closure part 7.

Figure 9:
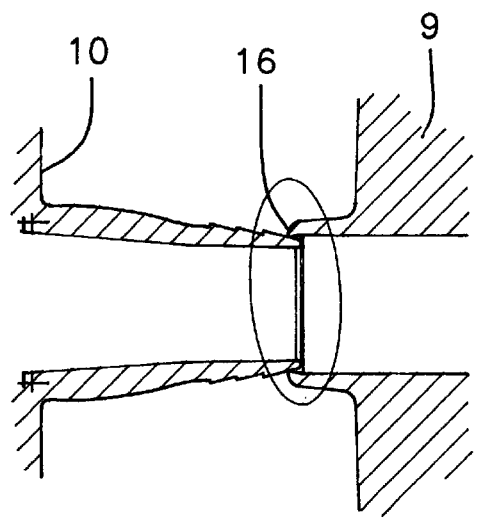
FIGS. 9 and 10 illustrate, on a larger scale, details of an embodiment of the invention shown in the encircled areas in FIGS. 1 and 9, respectively.
Figure 10:
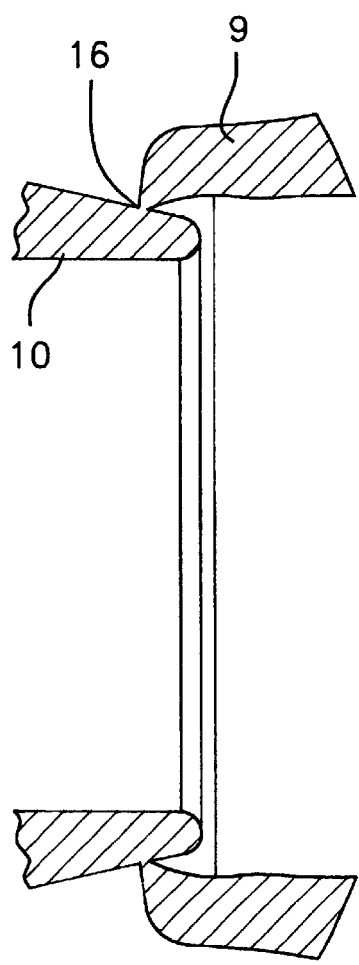

At its proximal end the hose member 4 is inseparably connected with an end member 9 which is detachably connected, e.g. by a notch-like incision in the same way as shown in FIG. 4, with a break-off compartment 10, in which the connector member 3 at the proximal end of the catheter 1 is accommodated. As an alternative, the detachable connection between the end member 9 and the compartment 10 may as shown in FIGS. 9 and 10 be provided by a weakening line 16 formed as a narrow bridge at the tip of the end member 9. After breaking-off the compartment 10, the connection between these two parts may be re-established by twisting and/or pushing the compartment 10 into the end member 9, whereby the tip of the end member 9 acts as a substantially liquid-tight seal against the outer surface of the compartment 10. It is noted in this respect that the outer diameter of at least the outer end portion of the compartment 10 is necessarily smaller than the inner diameter of the corresponding portion of the end member 9. At its open proximal end the compartment 10 is closed by a detachable cover 11.

In the embodiment shown the closure part 7 at the distal end of the hose member 4 as well as the end member 9 and the break-off compartment 10 are provided with relative large projecting gripping flanges 12 to facilitate operation of the catheter assembly for disabled users who may frequently suffer from a severely reduced dexterity.

In the illustrated preferred embodiment of the catheter assembly the catheter 1 is of the kind known per se, which is provided throughout the length of the catheter shaft intended for insertion into the urethra with a hydrophillic surface coating requiring preparation with a liquid swelling medium prior to use in order to attain a very slippery low-friction surface character which is desirable for inserting the catheter without causing any discomfort to the user.

By use of the catheter assembly according to the invention execution of the necessary preparation of the hydrophillic surface in a separate operation is avoided by integration of the amount of liquid swelling medium needed for the preparation in the package. As best shown in the cross-sectional view in FIG. 3 the liquid 13 is confined in the relatively narrow cavity of the hose member 4 surrounding the catheter shaft.

At manufacture the catheter 1 is simply arranged in the hose member package 4 together with the required amount of liquid followed by closure of the package by the cover 11 which hermetically closes the compartment 10 and thereby the proximal end of the package, the distal end of which has been hermetically closed by the connection of connector part 6 with the hose member 4. The liquid 13 will immediately act on the hydrophillic surface coating and thereby the catheter 1 will immediately be ready for use upon opening of the package.

Figure 5:
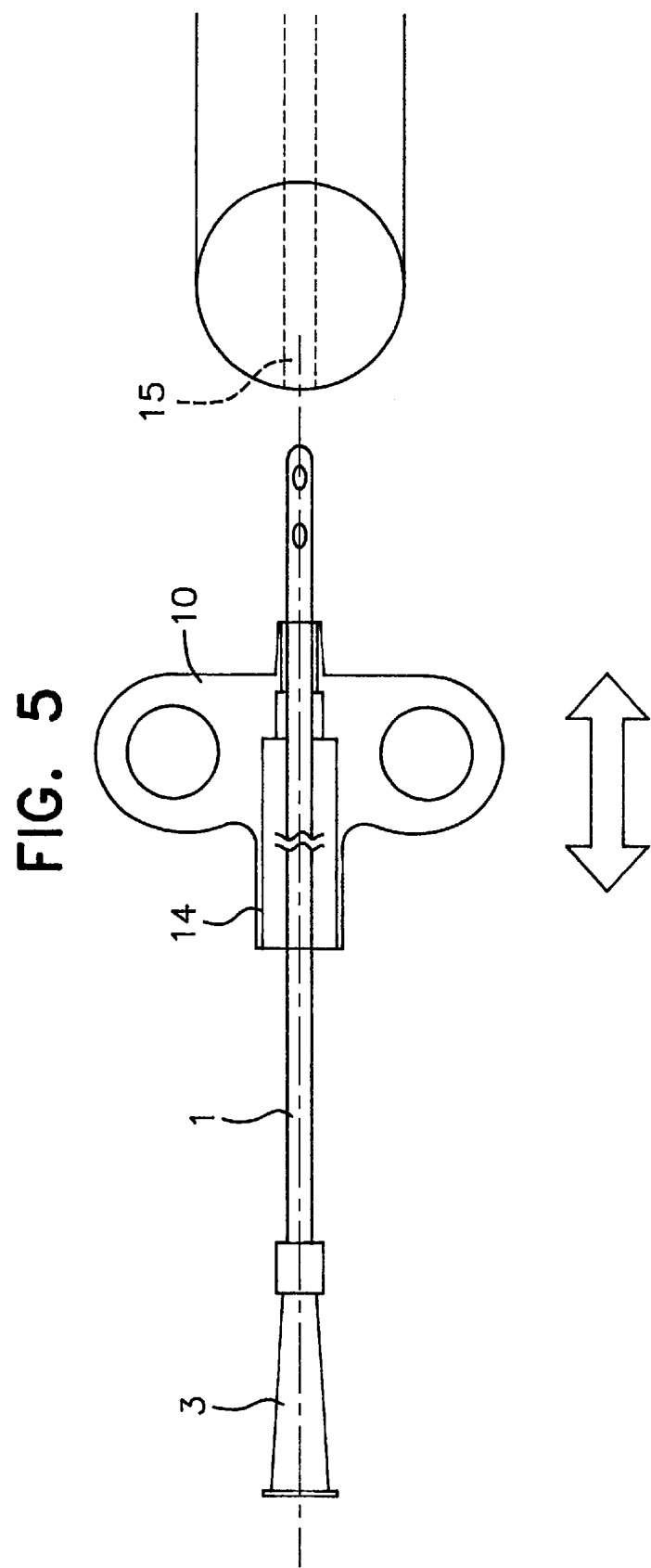

In the illustrated preferred embodiment non-contaminating insertion may be provided by using the compartment 10 which is formed with walls 14 of a thin flexible material as applicator for guided introduction of the catheter 1 into the urethra. This is achieved by breaking-off the compartment 10 from the end member 9 as shown in FIG. 4 and arranging the compartment 10 on the shaft of the catheter 1 as illustrated in FIG. 5. Due to the flexibility of the wall 14 of compartment 10 the compartment wall may be squeezed into engagement with the catheter 1 by a moderate finger pressure and guided introduction into the male urethra 15 illustrated by way of example may be performed without touching the catheter 1 directly.

Figure 7:
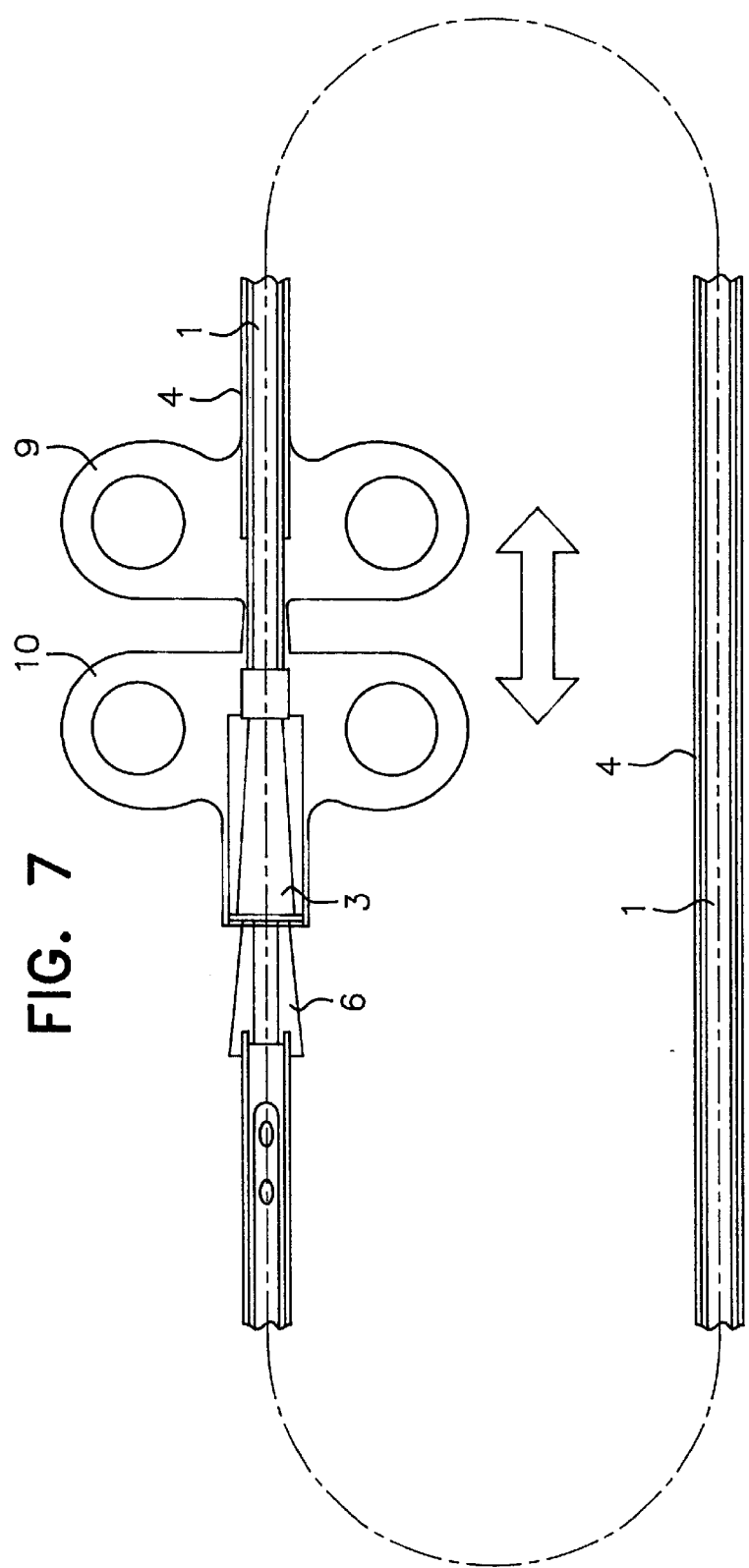
FIGS. 7 and 8 illustrate operation of the catheter assembly in FIG. 1 to form an extension of the catheter from the hose member package.
Figure 8:
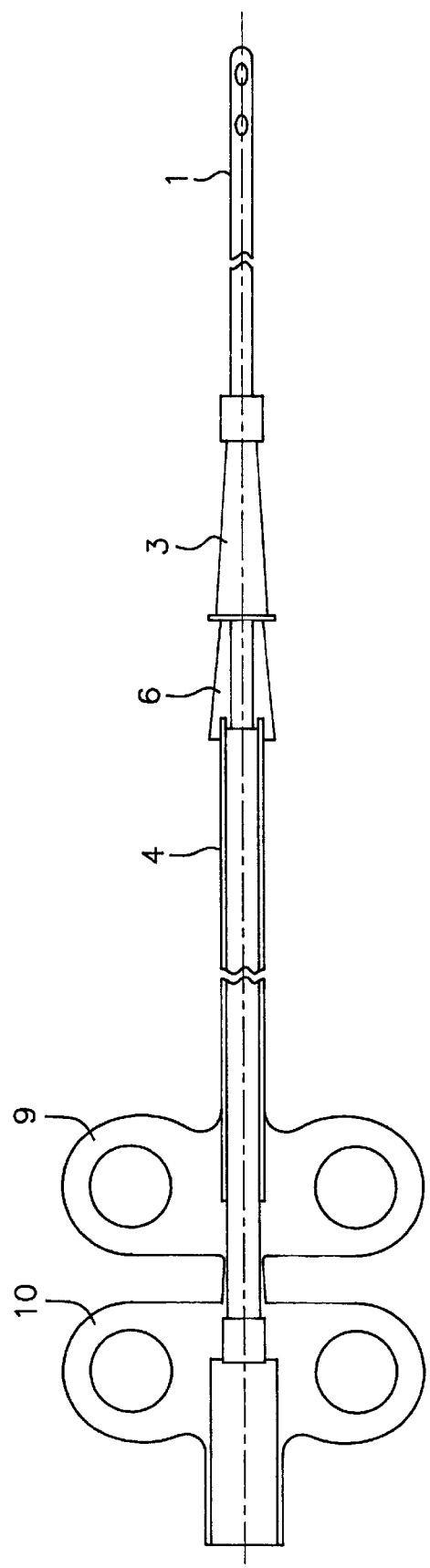

In the illustrated preferred embodiment the catheter assembly is prepared for use, as shown in FIGS. 7 and 8 by breaking-off the closure part 7 and removing the detachable cover 11. Due to the flexibility of the hose member 4 and the catheter 1 accommodated therein the proximal and distal ends of the package may now be brought together for connection of the connector member 3, which is inseparably connected with the catheter 1, with the connector part 6, which is inseparably connected with the distal end of the hose member 4.

Removal of the catheter 1 from the hose member 4 is now effected by separation of the connector member 3 from the compartment 10, whereby as shown in FIG. 8 the catheter 1 will be ready for insertion into the urethra.

Although preferred this additional catheter extension feature is not necessary for the use of compartment 10 as an insertion applicator as obtained by the present invention. Thus a separate additional hose member with a standard hose connector may be provided together with the catheter assembly for use as a catheter extension by connection of the standard hose connector with the proximal catheter end, or, in the embodiment shown in FIGS. 1 to 8, with the connector.

Equally the invention is not limited to use with a catheter having a hydrophillic surface coating, but may alternatively be used with conventional catheters of the kind requiring lubrication of the distal end before use. For this application a quantity of lubricant may be integrated in the package in a manner well known in the art.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

We claim:

1. A urinary catheter assembly comprising:
at least one urinary catheter having a proximal end;
a flexible tubular catheter package including a hose member with a cavity narrowly surrounding said at least one catheter, said package further including a tubular compartment connected with said hose member for accommodation of said proximal end of the at least one catheter, said compartment being closed in a first open end by a detachable cover member and, in a second opposite end, being detachably connected with said hose member, said compartment being further formed with walls of a thin flexible material so as to permit arrangement of said compartment on the at least one catheter for use as an applicator for guided non-contaminating insertion of the catheter into the urethra after detachment of said cover member and detachment of the compartment from the hose member.

2. The urinary catheter assembly as claimed in claim 1, wherein a distal end of the hose member remote from its connection with said compartment is closed by a detachable closure part said proximal end of the at least one catheter being formed for connection with said distal end of the hose member such that after removal of said closure part and detachment of said cover member, the hose member is connectable by its distal end with said proximal end of the at least one catheter to form an extension member in flow communication with the catheter.

3. The urinary catheter assembly as claimed in claim 1, wherein said proximal end of the at least one catheter is connected to a connector member that fits within said compartment.

4. The urinary catheter assembly as claimed in claim 2, wherein said proximal end of the at least one catheter is connected to a connector member and the distal end of the hose member is inseparably connected with a hose connector matching said connector member, said closure part being detachably connected with said hose connector.

5. The urinary catheter assembly as claimed in claim 1, wherein the hose member is, at a proximal end thereof, inseparably connected with an end member which is detachably connected with said compartment.

6. The urinary catheter assembly as claimed in claim 5, wherein the detachable connection is provided by a weakening line, and the connection between the compartment and the end member may be re-established by twisting and/or pushing the compartment into the end member, the weakening line forming a substantially liquid-tight seal.

7. The urinary catheter assembly as claimed in claim 1, wherein said catheter is provided on at least a part of its surface with a hydrophillic surface coating intended to produce a low-friction surface character of the catheter by treatment with a liquid swelling medium prior to use of the catheter, said package including an amount of said liquid swelling medium sufficient for said treatment of the hydrophillic catheter surface coating.

8. The urinary catheter assembly as claimed in claim 1, wherein said thin, flexible material of the walls of said compartment allows said walls to be squeezed with finger pressure into engagement with said catheter when said compartment is arranged thereon.

9. The urinary catheter assembly as claimed in claim 1, wherein said compartment may be slid axially along said catheter.

10. The urinary catheter assembly as claimed in claim 2, wherein at least one of said compartment and said closure part includes gripping flanges to facilitate insertion and use of said catheter.

11. The urinary catheter assembly as claimed in claim 5, wherein at least one of said compartment and said end member includes gripping flanges to facilitate insertion and use of said catheter.

12. A urinary catheter assembly comprising:

a urinary catheter having a proximal end inseparably connected to a connector member;

a flexible tubular catheter package including a hose member with a cavity narrowly surrounding said catheter, a connector part inseparably connected to a distal end of said hose member, and a tubular compartment for accommodating said proximal end of said catheter, said compartment being closed by a detachable cover member in a left open end and being detachably connected with said hose member in a second opposite end, said compartment having walls of a thin flexible material and, upon detachment from said hose member and detachment of said cover member, being arrangeable on said catheter for use as an applicator for guided non-contaminating insertion of the catheter into the urethra.

13. The urinary catheter assembly as claimed in claim 12, wherein a distal end of said connector part remote from its connection with said hose member, is closed by a detachable closure part, said connector member of said catheter being formed for connection with said connector part such that after removal of said closure part and detachment of said cover member, said connector part is connectable with said connector member to form an extension member in flow communication with the catheter.

14. The urinary catheter assembly as claimed in claim 12, wherein the hose member is, at a proximal end thereof, inseparably connected with an end member which is detachably connected with said compartment.

15. The urinary catheter assembly as claimed in claim 14, wherein the detachable connection between said end member and said compartment is provided by a weakening line, and the connection between the compartment and the end member may be re-established by twisting and/or pushing the compartment into the end member, the weakening line forming a substantially liquid-tight seal.

16. The urinary catheter assembly as claimed in claim 12, wherein said thin, flexible material of the walls of said compartment allows said walls to be squeezed with finger pressure into engagement with said catheter when said compartment is arranged thereon.

17. The urinary catheter assembly as claimed in claim 12, wherein said compartment may be slid axially along said catheter.

18. The urinary catheter assembly as claimed in claim 13, wherein at least one of said compartment and said closure part includes gripping flanges to facilitate insertion and use of said catheter.

19. The urinary catheter assembly as claimed in claim 14, wherein at least one of said compartment and said end member includes gripping flanges to facilitate insertion and use of said catheter.

20. The urinary catheter assembly as claimed in claim 13, wherein said thin, flexible material of the walls of said compartment allows said walls to be squeezed with finger pressure into engagement with said catheter when said compartment is arranged thereon.

* * * * *